(12) United States Patent
Kanade

(10) Patent No.: US 10,691,144 B2
(45) Date of Patent: Jun. 23, 2020

(54) SYSTEM FOR FLUID TESTING AND FUEL SUPPLY

(71) Applicant: Hrishikesh Dinkar Kanade, Maharashtra (IN)

(72) Inventor: Hrishikesh Dinkar Kanade, Maharashtra (IN)

( * ) Notice: Subject to any disclaimer, the term of this patent is extended or adjusted under 35 U.S.C. 154(b) by 129 days.

(21) Appl. No.: 15/647,496

(22) Filed: Jul. 12, 2017

(65) Prior Publication Data

US 2017/0329355 A1    Nov. 16, 2017

Related U.S. Application Data

(63) Continuation-in-part of application No. PCT/IB2016/050082, filed on Jan. 8, 2016.

(30) Foreign Application Priority Data

Jan. 12, 2015  (IN) ............................ 115/MUM/2015

(51) Int. Cl.
*G05D 7/06* (2006.01)
*G01N 21/25* (2006.01)
(Continued)

(52) U.S. Cl.
CPC ........... *G05D 7/0635* (2013.01); *B60K 15/03* (2013.01); *F02M 37/0076* (2013.01);
(Continued)

(58) Field of Classification Search
CPC ........ F02M 37/0076; B67D 2007/0446; B67D 7/78
See application file for complete search history.

(56) References Cited

U.S. PATENT DOCUMENTS 4,590,609 A * 5/1986 Chevalet ................. G06K 9/38
250/208.2
4,840,732 A * 6/1989 Rawlins ................. B01D 17/00
210/306

(Continued)

FOREIGN PATENT DOCUMENTS

EP           0647316 A1    4/1995
WO           94/25837 A1   11/1994

OTHER PUBLICATIONS

International Search Report and Written Opinion for International Application No. PCT/IB2016/050082, dated Apr. 26, 2016, 8 pages.

*Primary Examiner* — Angelisa L. Hicks
(74) *Attorney, Agent, or Firm* — Westman, Champlin & Koehler, P.A.

(57) ABSTRACT

A fluid testing system comprises a source that generates electromagnetic waves, a detector that receives the transmitted electromagnetic waves and generates analog signals corresponding to the colours represented in the electromagnetic waves and, a receptacle, having a fluid inlet and an optical inner tube with transparent walls. The receptacle is positioned between the source and the detector to enable the electromagnetic waves to pass through its walls and through a fluid sample in the receptacle. A repository stores a pre-determined range of reference values corresponding to the values of digital signals for fluids of various colours. An analog to digital converter in the system cooperates with the detector to receive the analog signals, converting them into digital signals, wherein the values are compared with the reference values by a comparator. A fluid outlet provides tested fluid. Further, a fuel supply system is disclosed for supplying fuel to a vehicle.

6 Claims, 6 Drawing Sheets

(51) Int. Cl.
*B60K 15/03* (2006.01)
*F02M 37/00* (2006.01)
*G01N 21/27* (2006.01)
*G01N 33/28* (2006.01)

(52) U.S. Cl.
CPC ........... *G01N 21/25* (2013.01); *G01N 21/255* (2013.01); *G01N 21/27* (2013.01); *G01N 33/2829* (2013.01); *B60K 2015/0321* (2013.01); *B60K 2015/03118* (2013.01); *B60K 2015/03203* (2013.01); *B60K 2015/03361* (2013.01); *G01N 2201/0627* (2013.01)

(56) References Cited

U.S. PATENT DOCUMENTS

| | | | |
|---|---|---|---|
| 5,078,901 A * | 1/1992 | Sparrow | F02M 37/24 210/744 |
| 5,528,363 A | 6/1996 | Fachinger et al. | |
| 5,654,497 A * | 8/1997 | Hoffheins | G01N 33/2829 702/27 |
| 5,715,052 A * | 2/1998 | Fujino | G01N 21/94 356/237.2 |
| 5,812,270 A | 9/1998 | Hampton et al. | |
| 6,422,061 B1 | 7/2002 | Sunshine et al. | |
| 7,473,352 B2 * | 1/2009 | Sundeng | B67D 7/76 15/246.5 |
| 7,644,889 B2 | 1/2010 | Johnson | |
| 2004/0025606 A1 * | 2/2004 | Veenstra | A01J 5/007 73/865.9 |
| 2005/0062344 A1 * | 3/2005 | Holt | B60R 25/23 303/7 |
| 2009/0112101 A1 * | 4/2009 | Furness, III | G01J 3/02 600/477 |
| 2009/0219512 A1 | 9/2009 | Myrick et al. | |

* cited by examiner

SYSTEM FOR FLUID TESTING AND FUEL SUPPLY

TECHNICAL FIELD

The present disclosure relates to the field of mechanical engineering. Particularly the present disclosure relates to automated fluid testing and fuel supply.

BACKGROUND

Vehicle engines can get damaged by the use of adulterated fuels. However, with the increase in fuel prices, the possibility of fuel being contaminated has also increased. There are numerous methods, systems and apparatuses of the present state of the art for testing fuel purity. Several countries have enacted laws for the use of fuel dyes, to identify different types of fuel. Fuel dyes are soluble in fuel and provide a specific color to fuel when mixed with it. For example, in India, petrol is dyed yellow and kerosene is dyed blue; if an adulterant, for example, on adding kerosene to an unadulterated petrol sample, the color of the resulting mixture becomes different from the color of the unadulterated petrol. Such adulterations can be identified by simple visual inspection. However, this technique of visual inspection cannot be relied upon to determine the purity or impurity of all types of fluids, as it is majorly dependent on subjective interpretation. Moreover, interpretations based on visual results may vary, depending on an interpreter's experience, and on insufficient or excessive illumination on the fluid samples.

Therefore, there is a need of a fluid testing system that mitigates the aforementioned drawbacks of visual inspection of the fluid to be tested.

OBJECTS

Some of the objects of the present disclosure aimed to ameliorate one or more problems of the prior art or to at least provide a useful alternative are listed herein below.

An object of the present disclosure is to provide a fluid testing system.

Yet another object of the present disclosure is to provide a fluid testing system that requires comparatively less skilled labor for operation.

Still another object of the present disclosure is to provide a fluid testing system which reduces manual effort and the time required for testing.

An additional object of the present disclosure is to provide a fluid testing system which does not require visual inspection for determining purity and impurity of fluids.

Still another object of the present disclosure is to provide a fuel testing module for testing the adulteration level of fuel.

Still another object of the present disclosure is to provide a fuel supply system for supplying fuel to a vehicle.

Other objects and advantages of the present disclosure will be more apparent from the following description when read in conjunction with the accompanying figures, which are not intended to limit the scope of the present disclosure.

SUMMARY

The present disclosure envisages a fluid testing system. The system comprises a source, a detector, a receptacle, a repository, an analog to digital converter and a comparator. The source is configured to generate electromagnetic waves and the detector is configured to receive electromagnetic waves transmitted by the source and generate analog signals corresponding to the colours represented in the electromagnetic waves. The receptacle has a fluid inlet and an optical inner tube having transparent walls, said receptacle is positioned between the source and the detector. The receptacle is configured to enable the electromagnetic waves to pass through its walls and through a fluid sample filled in the receptacle. The repository is configured to store a predetermined range of reference values corresponding to the values of digital signals for fluids of various colours. The analog to digital converter is configured to cooperate with the detector to receive the analog signals and convert them into digital signals. The comparator is configured to receive the digital signals and compare the values of digital signals with the reference values to determine the colour values of the fluid sample, thereby determining the adulteration level of the fluid. The fluid testing system comprises a fluid outlet for providing tested fluid.

Further, the receptacle has an opaque housing covering the receptacle. The housing has at least one first hole for placement of the source and at least one second hole for placement of the detector, against the transparent walls of the optical inner tube.

In one embodiment, the source can be at least one light emitting diode. In another embodiment, the detector can be at least one selected from the group consisting of photodiode, optical sensor and radiation camera.

In yet another embodiment, the system includes a display configured to display the adulteration level of the fluid.

The present disclosure also envisages a fuel supply system for supplying fuel to a fuel tank of a vehicle. The fuel supply system further comprises a fuel testing module configured to determine adulteration level of fuel. The fuel supply system comprises a fuel inlet for supplying fuel to said fuel testing module. The system also comprises a fuel outlet for providing tested fuel from the fuel testing module. The system comprises an auxiliary tank. The system further comprises a fuel diverter configured to receive fuel from said fuel outlet and selectively divert fuel either to the fuel tank or to the auxiliary tank. Typically, the fuel diverter is a valve.

The system further comprises a controller configured to direct the fuel diverter to divert fuel to the fuel tank or to the auxiliary tank based on the adulteration level of fuel determined by the fuel testing module. In accordance with an embodiment, the controller directs the fuel diverter to divert non-adulterated fuel to the fuel tank and divert adulterated fuel to the auxiliary tank. Further, the system comprises a pump configured to receive fuel from the fuel diverter and pump it further to the fuel tank.

Typically, the auxiliary tank has an opening configured to drain out fuel received therein.

Further in an embodiment, the fuel testing module comprises a source configured to generate electromagnetic waves. The fuel testing module further comprises a detector configured to receive electromagnetic waves transmitted by the source and generate analog signals corresponding to the colours represented in the electromagnetic waves. Further, the module comprises a receptacle, having an optical inner tube having transparent walls, wherein said receptacle is positioned between said source and said detector, wherein the receptacle is configured to receive fuel. Further, the module comprises a repository configured to store a predetermined range of reference values corresponding to the values of digital signals for fuel of various colours. The fuel testing module also comprises an analog to digital converter configured to cooperate with said detector to receive the analog signals and convert them into digital signals. In accordance with the present embodiment, the fuel testing module comprises a comparator configured to receive said digital signals and compare the values of digital signals with said reference values to determine colour values of fuel thereby determining adulteration level of fuel. Furthermore, the fuel testing module comprises a display configured to indicate the adulteration level of fuel.

In an embodiment, the receptacle has an opaque housing covering the receptacle, wherein said housing has at least one first hole for placement of said source and at least one second hole for placement of said detector, against the transparent walls of the optical inner tube.

In another embodiment, when the controller and the fuel diverter are in an inoperative configuration, the fuel diverter is locked to permit the flow of fuel only to the fuel tank.

This summary is provided to introduce concepts related to the fluid testing system, which is further described below in the detailed description. This summary is neither intended to identify essential features of the present disclosure nor is it intended for use in determining or limiting the scope of the present disclosure.

BRIEF DESCRIPTION OF ACCOMPANYING DRAWING

The system of the present disclosure will now be described with the help of the non-limiting accompanying drawing, wherein the accompanying drawings are not to scale, in which.

Figure 1:
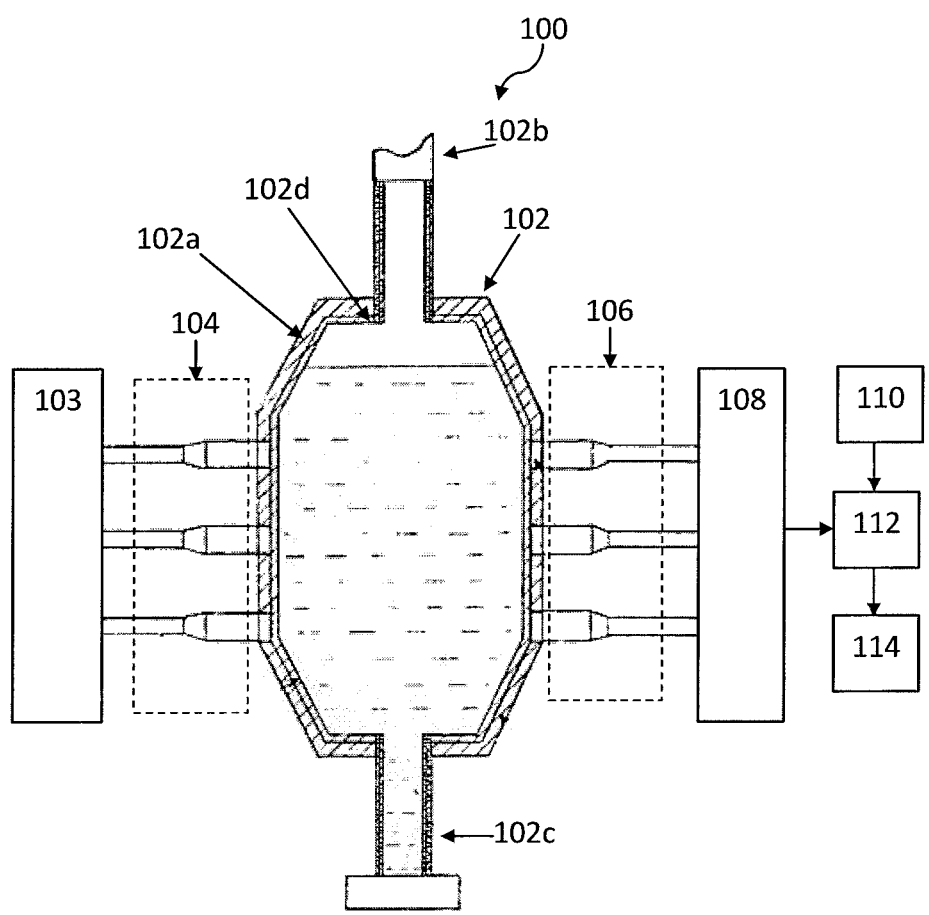
FIG. 1 illustrates a schematic cross sectional representation of the fluid testing system in accordance with one embodiment of the present disclosure.
Figure 2:
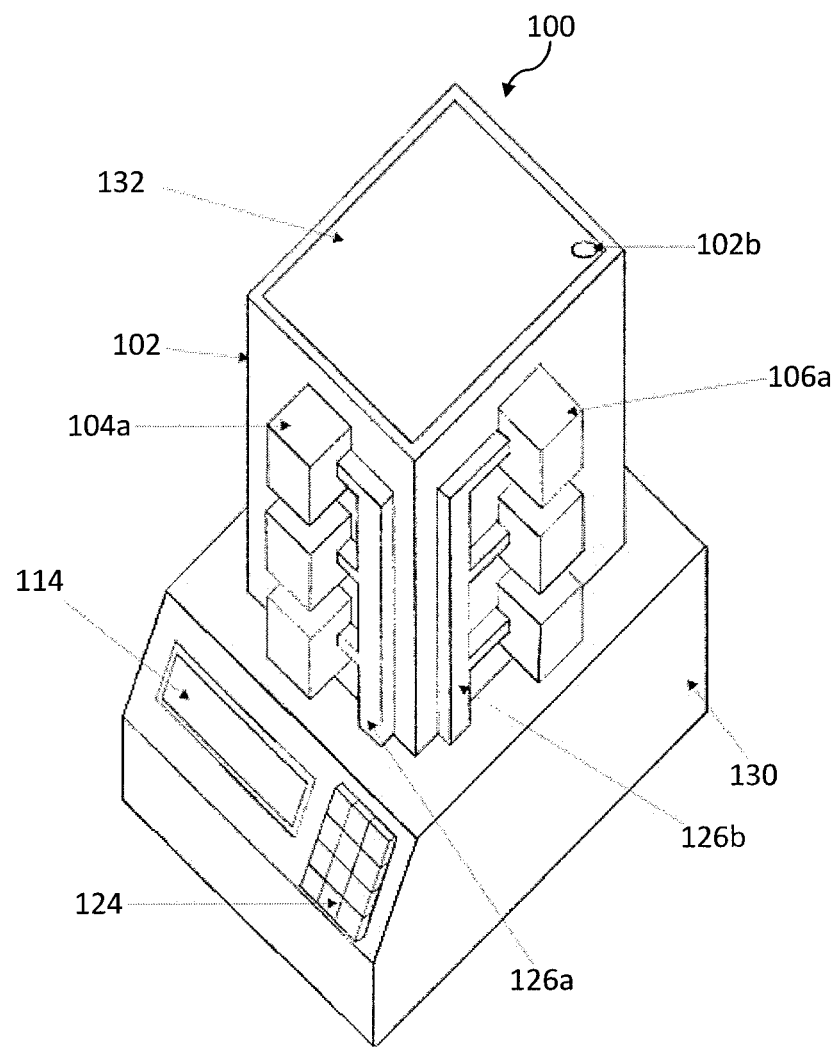
FIG. 2 illustrates a schematic perspective representation of a fluid testing system in accordance with another embodiment of the present disclosure.
Figure 4A:
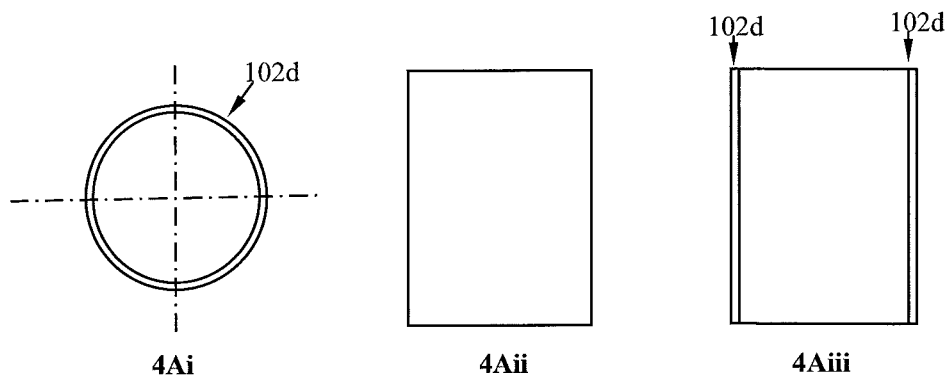
Figure 4B:
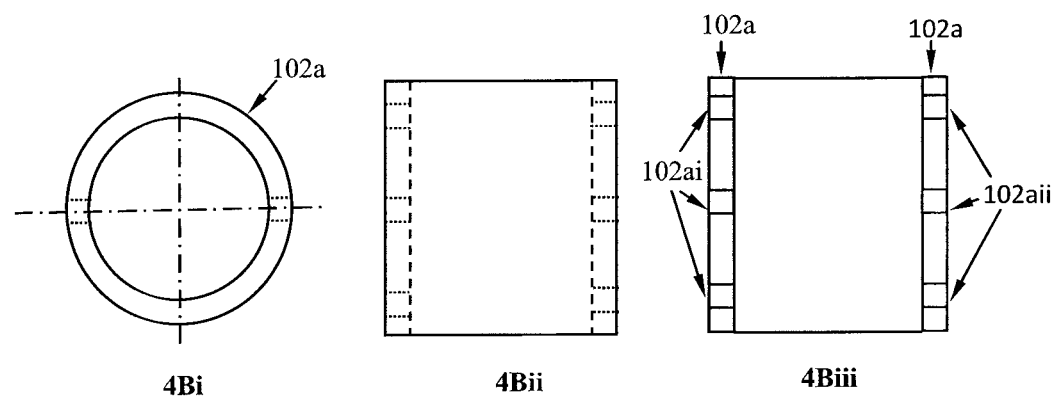
Figure 4C:
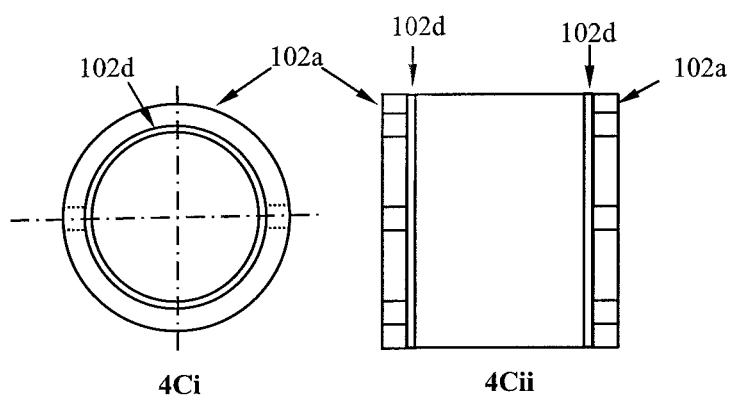
Figure 5:
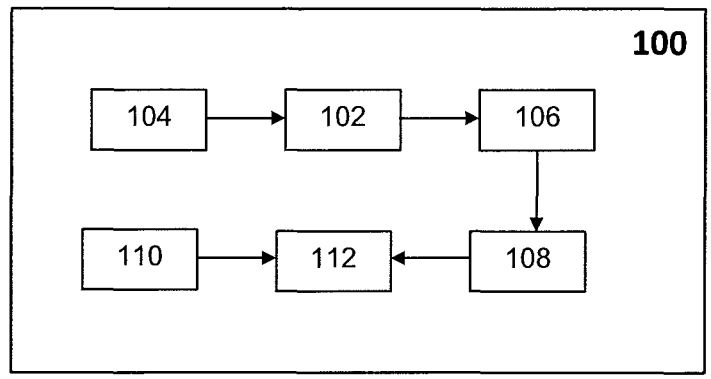
Figure 6:
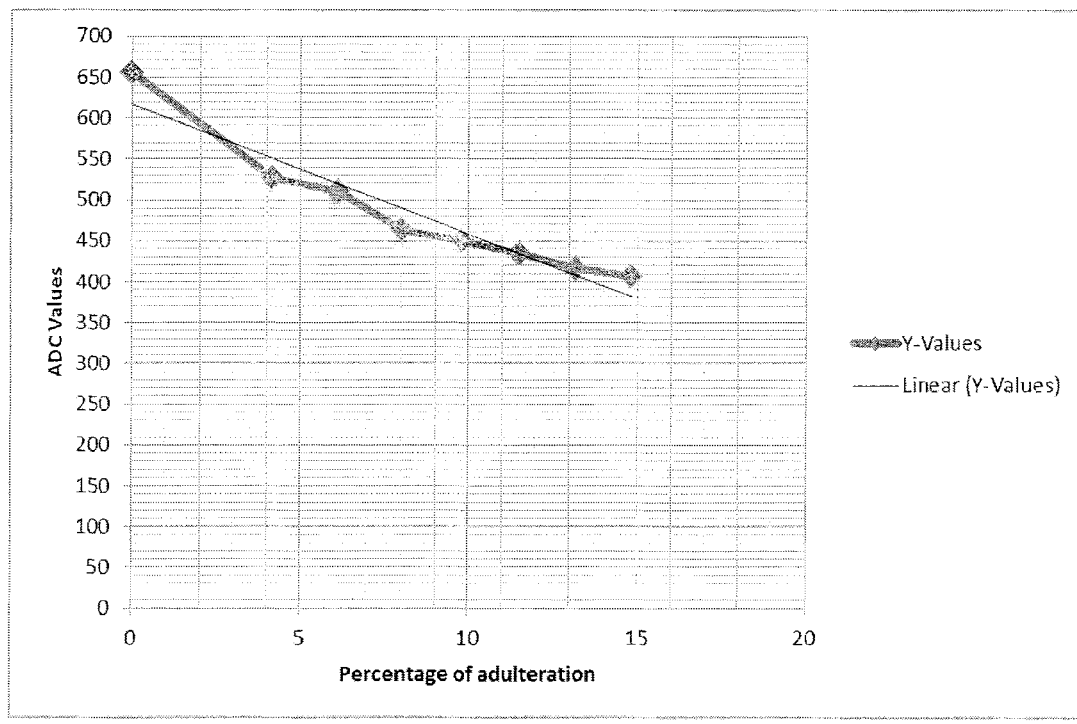
Figure 7:
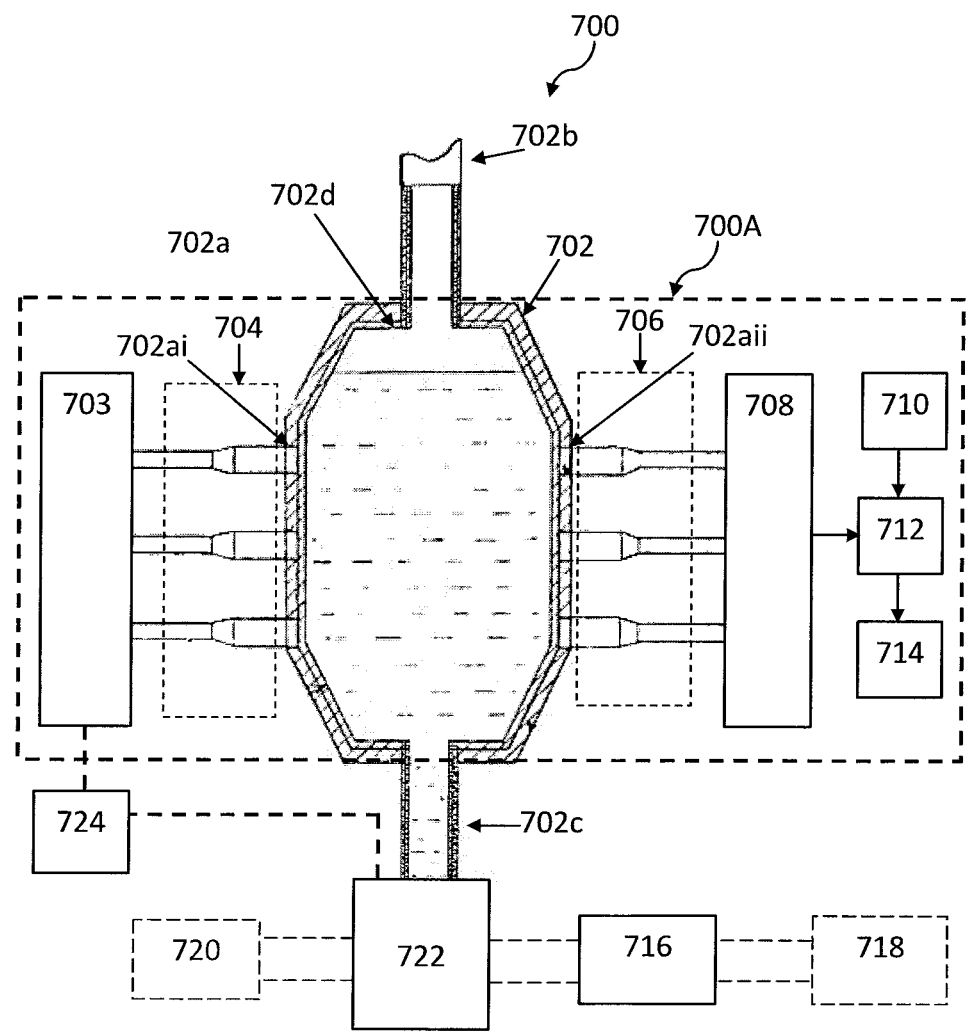

FIG. 4Ai illustrates a top view of an optical inner tube of a receptacle of the fluid testing system of FIG. 1 & FIG. 2;

FIG. 4Aii illustrates a front view of an optical inner tube of a receptacle of the fluid testing system of FIG. 1 & FIG. 2;

FIG. 4Aiii illustrates a cross-sectional front view of an optical inner tube of a receptacle of the fluid testing system of FIG. 1 & FIG. 2;

FIG. 4Bi illustrates a top view of a non-optical outer tube/housing of the receptacle of FIG. 1 & FIG. 2;

FIG. 4Bii illustrates a front view of a non-optical outer tube/housing of the receptacle of FIG. 1 & FIG. 2;

FIG. 4Biii illustrates a cross-sectional front view of a non-optical outer tube/housing of the receptacle of FIG. 1 & FIG. 2;

FIG. 4Ci illustrates an assembled top view of the optical inner tube and the non-optical outer tube/housing of FIG. 1 & FIG. 2;

FIG. 4Cii illustrates an assembled cross sectional front view of the optical inner tube and the non-optical outer tube/housing of FIG. 1 & FIG. 2;

FIG. 5 illustrates a block schematic of an embodiment of a fluid testing system in accordance with the present disclosure;

FIG. 6 illustrates a graphical observation of values of an analog to digital converter of the system of the present disclosure for different adulteration percentages in fluid; and FIG. 7 illustrates a schematic cross-sectional representation of a fuel supply system for a vehicle in accordance with an embodiment of the present disclosure.

DETAILED DESCRIPTION

The system of the present disclosure will now be described with reference to the embodiment shown in the accompanying drawing. The embodiment does not limit the scope and ambit of the disclosure. The description relates purely to the example and the preferred embodiment of the disclosed system and its suggested application.

The system and the various features and advantageous details thereof are explained with reference to the non-limiting embodiment in the following description. Descriptions of well-known parameters and processing techniques are omitted so as to not unnecessarily obscure the embodiment herein. The examples used herein are intended merely to facilitate an understanding of ways in which the embodiment herein may be practiced and to further enable those of skill in the art to practice the embodiment herein. Accordingly, the examples should not be construed as limiting the scope of the embodiment herein.

Figure 3:
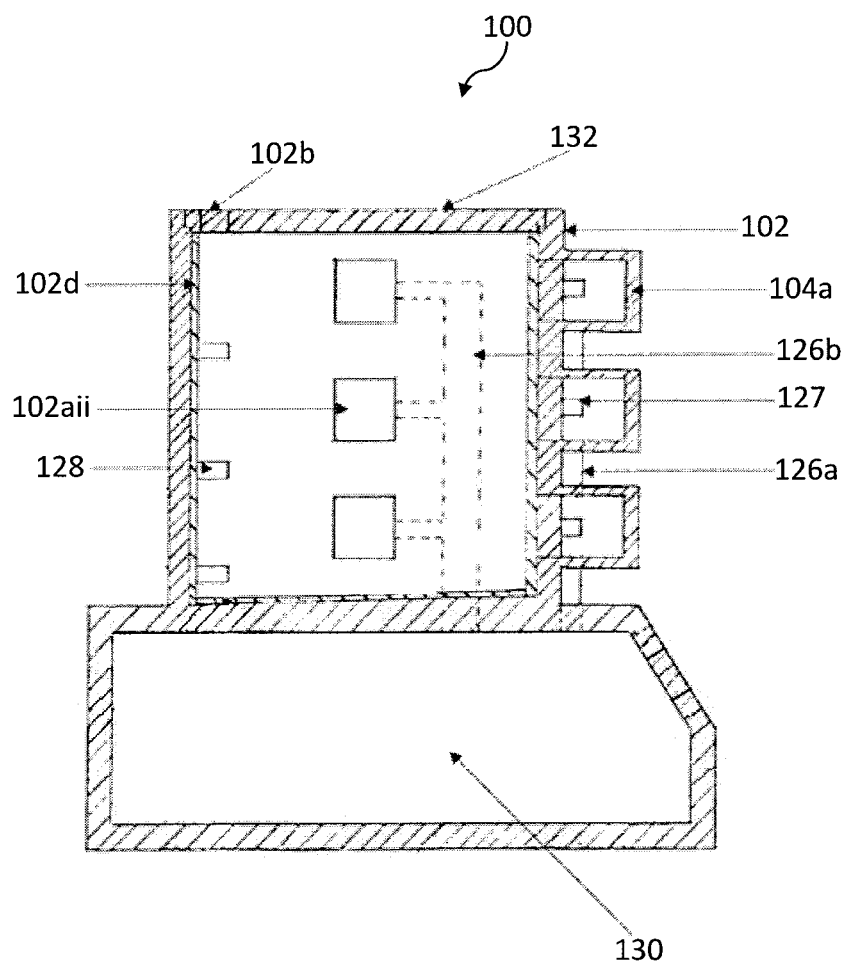
FIG. 3 illustrates a schematic cross sectional representation of the fluid testing system of FIG. 2.

To limit the drawbacks of the conventional visual interpretation method of testing the purity of fluids, the present disclosure envisages a fluid testing system. Referring to the accompanying drawing, FIG. 1 to FIG. 3 illustrate schematic representations of the fluid testing system 100 in accordance with the embodiments of the present disclosure and FIG. 5 illustrates a block schematic of an embodiment of a fluid testing system 100 in accordance with the present disclosure. FIG. 2 illustrates a fluid testing system 100 that can be used as a kit to test fluid samples for purity and impurity. The fluid testing system 100 includes a receptacle 102, a source 104, a detector 106, a repository 110, an analog to digital converter 108 and a comparator 112.

The source 104 is configured to generate electromagnetic waves and the detector 106 is configured to receive the electromagnetic waves transmitted by the source 104 and generate analog signals corresponding to the colours represented in the electromagnetic waves. In one embodiment, the source 104 is a plurality of radiation sources and the detector 106 is a plurality of detectors/sensors. The receptacle 102, in an embodiment, has a fluid inlet 102b and an optical inner tube having transparent walls 102d. The receptacle 102 is positioned between the source 104 and the detector 106 such that the electromagnetic waves transmitted by the source 104 pass through the receptacle walls and through a fluid sample filled in the receptacle 102.

In one embodiment, the receptacle 102 has an optical inner tube having transparent walls 102d as illustrated in FIG. 4Ai, FIG. 4Aii and FIG. 4Aiii. The receptacle 102 has an opaque housing 102a covering the receptacle 102, which is a non-optical outer tube, as illustrated in FIG. 4Bi, FIG. 4Bii and FIG. 4Biii. FIG. 4Ci and FIG. 4Cii illustrate the housing 102a which surrounds the optical inner tube with transparent walls 102d of the receptacle 102. The optical inner tube 102d is made of a transparent material that allows passage of electromagnetic waves (light waves) therethrough and the housing 102a is made of an opaque material that prevents passage of surrounding light waves therethrough. The housing 102a is configured with at least one first hole 102ai for placement of the source 104 and at least one second hole 102aii for placement of the detector 106, against the transparent walls of the optical inner tube 102d. The fluid testing system 100 comprises a fluid outlet 102c for providing tested fluid.

The source 104 according to one embodiment of the present disclosure is a plurality of light emitting diodes (LED's) such as LED's. Although the present disclosure is described by using three LED's as the source 104, the present disclosure is not limited to the use of LED's as the source 104 and less or more than three of LED's may be used. Each LED is fitted to the first hole 102*ai*, typically by at least one first wire (not illustrated in Figures). The source 104 is controlled by a controller 103 to generate electromagnetic waves that pass through the receptacle 102 containing a fluid sample. These waves are received by the detector 106. The detector 106 according to one embodiment of the present disclosure can be a plurality of photodiodes or a plurality of radiation cameras or a plurality of optical sensors. Although the present disclosure is described by using three photodiodes or radiation cameras or optical sensors as the detector 106, the present disclosure is not limited to the use of photodiodes or radiation cameras or optical sensors as a radiation detector and less or more than three photodiodes or radiation cameras or optical sensors may be used. The photodiodes or radiation cameras are fitted to the second holes 102*aii*, typically by at least one second wire (not illustrated in Figures). The detector 106 is located such that the receptacle 102 is disposed between the source 104 and the detector 106. The detector 106 may be positioned exactly opposite to the source 104 or at an inclination. The detector 106 detects electromagnetic waves passing through the optical inner tube with transparent walls 102*d* filled with fluid, and generates analog signals corresponding to the colours represented in the electromagnetic waves. The analog to digital converter 108 cooperates with the detector 106 to receive the analog signals and convert them into digital signals. The repository 110 stores a pre-determined range of reference values corresponding to the values of digital signals for fluids of various colours. In accordance with fluid standards or by previous experiments, a range of reference values of pure fluid is determined and stored in the repository 110 and/or a range of values of impure fluid is determined and stored in the repository 110. These ranges vary based on the types of fluids. In one embodiment the range of reference values can be selected by users based on fluids to be tested. The present disclosure is described by considering that the repository 110 stores a pre-determined range of reference values corresponding to that of pure fluid. However, the present disclosure is not limited to the repository 110 storing pre-determined range of values corresponding to that of pure fluid. The comparator 112 receives the digital signals from the analog to digital convertor 108 and compares these values of digital signals with the reference values stored in the repository 110 to determine the colour values of the fluid sample, thereby determining adulteration level of the fluid. In one embodiment, if the set of values is within the range of the stored pre-determined reference values, then the fluid is pure fluid and if the set of values is not within the range of the stored pre-determined values then fluid is impure. In another embodiment, if the fluid is impure, the system 100 provides the percentage of adulteration in the fluid. This adulteration level of fluid is displayed on a display 114. In one embodiment, the display 114 displays that the fluid is pure or impure and if impure, it displays the approximate level of adulteration.

In an embodiment, a signal conditioning circuit (not shown in Figures) accepts the analog output signal of the detector 106 as input and manipulates the analog signal to meet the input requirements of the analog to digital converter 108. The signal conditioning circuit may perform functions such as amplification, conversion and any other processes required to make the output of detector 106 meet the input requirements of the analog to digital converter 108. The analog to digital converter 108 accepts the output signal of the signal conditioning circuit as input.

Further, in one embodiment, the source 104 is controlled by a controller 103 and is powered by a power source (not illustrated in Figures), typically a battery which may be pre-existing in the system 100 or may be separately provided and fitted with the system 100 or in the vehicle. Typically, the controller is a micro-controller. In one embodiment, the fluid testing system 100 may include indicators (not illustrated in Figures). Typically, the indicators are light emitting diodes (LED's). The indicators indicate status of the fluid testing system 100 such that the LED flashes a red light to indicate that fluid is impure, a green light to indicate that fluid is pure and a white light to indicate that the fluid testing is in process. As the fluid testing system 100 automatically indicates pure and impure fluid by the indicators, it requires comparatively less skilled labor for operation. In an embodiment where the fluid testing system 100 is used as a kit, the receptacle 102 is mounted on a base 130. The base 130 houses the analog to digital converter 108, repository 110, comparator 112 and other electronic devices required for testing fluid samples. In one embodiment, the base 130 also houses the power supply. The fluid testing system 100 includes a plurality of buttons 124 which are to be used as control inputs. In another embodiment, the fluid testing system 100 includes a source housing 104*a* for the source 104, source wire paths 126*a* for carrying wires from the source 104 to base 130, a detector housing 106*a* for the detector 106, detector wire paths 126*b* for carrying wires from the detector 106 to base 130, openings 127 for wires to enter the receptacle 102, a removable top cover 132 for making any maintenance work possible, guide loops 128 integrated into the transparent wall of the receptacle 102 for holding a fluid pipe in place through which a fluid sample is collected, first holes 102*aI* through which the electromagnetic waves can enter the receptacle 102 from the source 104 and second holes 102*aii* through which the electromagnetic waves can fall from the receptacle 102 on the detector 106. In one embodiment, fluid sample is provided in the receptacle 102 through the fluid inlet 102*b* and test is initiated by entering a start command via buttons 124. When the testing starts, the source 104 for the top layer is turned on and the reading from the detector 106 at same layer is taken. After receiving the reading the source 104 is turned off. The same procedure is repeated for each layer, and after readings from all the layers are received, the received readings are compared with the stored reference values, and approximate level of adulteration, and possible adulterants are displayed on the display 114. In an embodiment, control inputs provided by the buttons 124 are a power switch, reset switch, and other switches as per the requirement. Once the testing finishes, in one embodiment, the fluid sample is removed from the receptacle 102 through the fluid inlet 102*b*.

Referring to the accompanying drawing, FIG. 6 illustrates a graphical observation of values of an analog to digital converter of the system of the present disclosure for different adulteration percentages in fluid. For this observation, an ADC (analog to digital converter) having 12-bit resolution is used. The fluid sample to be tested is petrol to which kerosene is added as an adulterant. The percentage of adulteration is varied to note its effect on the analog to digital converter values. Table 1 given below shows the ADC values for different adulteration percentages:

TABLE 1

| Percentage of adulteration | 12-bit ADC value |
| --- | --- |
| 0% (Pure petrol) | 655 |
| 4.17% | 527 |
| 6.12% | 511 |
| 8% | 463 |
| 9.8% | 449 |
| 11.53% | 435 |
| 13.2% | 417 |
| 14.8% | 407 |

It is observed from FIG. 6 as well as Table 1 that the ADC values decrease with increase in percentage of adulteration.

In one embodiment, the system 100 of the present disclosure is used for testing any fluid which is transparent or translucent and shows change in color when adulterated or degraded (spoiled, rotten, or not prepared properly such as beverages). For example, in case of a hydraulic fluid line, the system 100 illustrated in FIG. 1 is constructed from appropriate materials to handle the operating pressure of the hydraulic system so as to continuously monitor the quality of the fluid. Additionally, the system 100 can also be introduced in pipe carrying coolant fluids for monitoring the quality of the fluids. Also, the system 100 can be placed in a delivery pipe for beverages and at intervals, to stop the flow of fluid and check the quality of a fluid sample. The flow is then allowed to pass through if the quality is satisfactory or the delivery system is halted if the quality is not as expected in order to diagnose the problem.

In accordance with another embodiment and with reference to FIG. 7, a fuel supply system 700 is provided for supplying fuel to a fuel tank 718 of a vehicle. The fuel supply system 700 comprises a fuel testing module 700A configured to determine adulteration level of fuel. The fuel supply system 700 further comprises a fuel inlet 702b for supplying fuel to said fuel testing module 700A. The fuel supply system 700 further comprises a fuel outlet 702c for providing tested fuel from the fuel testing module 700A. The fuel supply system 700 comprises an auxiliary tank 720. The fuel supply system 700 further comprises a fuel diverter 722 configured to receive fuel from said fuel outlet 702c and selectively divert fuel either to the fuel tank 718 or to the auxiliary tank 720. Typically, the fuel diverter 722 is a valve.

Further, the fuel supply system 700 comprises a controller 724 configured to direct the fuel diverter 722 to divert fuel to the fuel tank 718 or to the auxiliary tank 720 based on the adulteration level of fuel determined by the fuel testing module 700A. Typically, the controller 724 directs the fuel diverter 722 to divert non-adulterated fuel to the fuel tank 718 and divert adulterated fuel to the auxiliary tank 720. Typically, the controller 724 controls ports of a valve of the fuel diverter 722 to direct flow of fuel to the fuel tank 718 or to the auxiliary tank 720.

Furthermore, the system 700 comprises a pump 716 configured to receive fuel from the fuel diverter 722 and pump it further to the fuel tank 718, wherein fuel pumped to the fuel tank 718 is non-adulterated in nature. In accordance with the present embodiment, the pump 716 is fitted between the fuel diverter 722 and the fuel tank 718. Typically, the pump 716 is unidirectional in nature.

In accordance with an embodiment, the auxiliary tank 720 has an opening configured to drain out fuel received therein. In one embodiment, when the controller 724 and the fuel diverter 722 are in an inoperative configuration, the fuel diverter 722 is locked to permit the flow of fuel only to the fuel tank 718.

The fuel testing module 700A further comprises a source 704 configured to generate electromagnetic waves. Further, in one embodiment, the source 704 is controlled by a main controller 703 and is powered by a power source (not illustrated in Figures), typically a battery which may be pre-existing in the system 700 or may be separately provided and fitted with the system 700 or in the vehicle. Typically, the main controller 703 is a micro-controller. In accordance with another embodiment, the controller 724 is an auxiliary controller or forms part of the main controller 703. The electromagnetic waves transmitted by the source 704 are received by a detector 706 such that the detector 706 generates analog signals corresponding to the colours represented in the electromagnetic waves.

The fuel testing module 700A further comprises a receptacle 702, having an optical inner tube having transparent walls 702d. The optical inner tube with transparent walls 702d is made of a transparent material that allows passage of electromagnetic waves (light waves) therethrough. The receptacle 702 is positioned between said source 704 and said detector 706 wherein the receptacle 702 is configured to receive fuel.

In one embodiment, the receptacle 702 has an opaque housing 702a covering the receptacle 702, said housing 702a made of an opaque material that prevents passage of surrounding light waves therethrough. In an embodiment, the housing 702a has at least one first hole 702a1 for placement of said source 704 and at least one second hole 702aii for placement of said detector 706, against the transparent walls of the optical inner tube 702d.

In one embodiment, the fuel testing module 700A comprises a repository 710 configured to store a pre-determined range of reference values corresponding to the values of digital signals for fuel of various colours. In one embodiment, the fuel testing module 700A further comprises an analog to digital converter 708 configured to cooperate with said detector 706 to receive the analog signals and convert them into digital signals. In accordance with an embodiment, the fuel testing module 700A comprises a comparator 712 configured to receive said digital signals and compare the values of digital signals with said reference values to determine colour values of fuel thereby determining adulteration level of fuel. In accordance with an embodiment, a display 714 is configured to indicate the adulteration level of fuel.

In one embodiment, the fuel testing module 700A may include indicators (not illustrated in Figures). Typically, the indicators are light emitting diodes (LED's). The indicators indicate status of the fuel testing module 700A such that the LED flashes a red light to indicate that fuel is adulterated, a green light to indicate that fuel is non-adulterated and a white light to indicate that the fuel testing is in process. As the fuel testing module 700A automatically indicates non-adulterated and adulterated fuel by the indicators, it requires comparatively less skilled labor for operation.

Technical Advancements

The technical advancements offered by the present disclosure include the realization of:

- a fluid testing system;
- a fluid testing system that requires comparatively less skilled labor for operation;
- a fluid testing system which reduces manual effort and the time required for testing;
- a fluid testing system which does not require visual inspection for determining purity and impurity of fluid;

a fuel testing module which when fitted in a vehicle, prevents adulterated fuel from entering the vehicle, thus avoiding any damage to the vehicle due to adulterated fuel; and a fuel supply system for supplying fuel to a vehicle.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A fuel supply system for supplying fuel to a fuel tank of a vehicle, said system comprising:
    a fuel testing module including:
        a source configured to generate electromagnetic waves;
        a detector configured to receive electromagnetic waves transmitted by the source and generate analog signals corresponding to the colours represented by the electromagnetic waves refracted by the fuel;
        a receptacle, having an optical inner tube with transparent walls, said receptacle positioned between said source and said detector, said receptacle configured to receive fuel;
        a repository configured to store a pre-determined range of reference values corresponding to the values of digital signals for fuel of various colours;
        an analog to digital converter configured to cooperate with said detector to receive the analog signals and convert them into digital signals;
        a comparator configured to receive said digital signals and compare the values of digital signals with said reference values to determine colour values of fuel thereby determining adulteration level of fuel; and
        a display configured to indicate the adulteration level of fuel;
    a fuel inlet for supplying fuel to said fuel testing module;
    a fuel outlet for providing tested fuel from the fuel testing module;
    an auxiliary tank;
    a fuel diverter configured to receive fuel from said fuel outlet and selectively divert fuel either to the fuel tank or to the auxiliary tank;
    a controller configured to direct the fuel diverter to divert fuel to the fuel tank or to the auxiliary tank based on the adulteration level of fuel determined by the fuel testing module; and
    a pump configured to receive fuel from the fuel diverter and pump it further to the fuel tank.

2. The system as claimed in claim 1, wherein the receptacle has an opaque housing covering the receptacle, said housing having at least one first hole for placement of said source and at least one second hole for placement of said detector, against the transparent walls of the optical inner tube.

3. The system as claimed in claim 1, wherein said fuel diverter is a valve.

4. The system as claimed in claim 1, wherein said controller directs the fuel diverter to divert non-adulterated fuel to the fuel tank and divert adulterated fuel to the auxiliary tank.

5. The system as claimed in claim 1, wherein said auxiliary tank has an opening configured to drain out fuel received therein.

6. The system as claimed in claim 1, wherein when the controller and the fuel diverter are in an inoperative configuration, the fuel diverter is locked to permit the flow of fuel only to the fuel tank.

* * * * *